(12) United States Patent
Jones et al.

(10) Patent No.: US 7,229,286 B2
(45) Date of Patent: Jun. 12, 2007

(54) COMPOSITE VENEERED CAST GLASS-CERAMIC DENTAL CONSTRUCT

(76) Inventors: Derek W. Jones, 980 Ivanhoe Street, Halifax, Nova Scotia (CA) B3H 2X1; Amin S. Rizkalla, 146 Orkney Crescent, London, Ontario (CA) N5X 3R5; Gordon C. Hall, 6 Argus Drive, Dartmouth N.S. (CA) B3A 4Y9

( * ) Notice: Subject to any disclaimer, the term of this patent is extended or adjusted under 35 U.S.C. 154(b) by 0 days.

(21) Appl. No.: 10/098,104

(22) Filed: Aug. 5, 2002

(65) Prior Publication Data

US 2002/0197583 A1   Dec. 26, 2002

Related U.S. Application Data

(63) Continuation of application No. 09/838,953, filed on Apr. 20, 2001, now abandoned.

(51) Int. Cl.
*A61C 13/08* (2006.01)
(52) U.S. Cl. .................................. 433/212.1
(58) Field of Classification Search ............ 433/228.1, 433/218, 219, 222.1, 212.1; 106/35
See application file for complete search history.

(56) References Cited

U.S. PATENT DOCUMENTS

| | | | | |
|---|---|---|---|---|
| 3,951,670 A * | 4/1976 | Bush | .............................. | 501/7 |
| 4,017,454 A * | 4/1977 | Muller | ......................... | 523/117 |
| 4,028,325 A | 6/1977 | King et al. | .................... | 260/42 |
| 4,189,325 A | 2/1980 | Barrett et al. | .................. | 106/35 |
| 4,364,731 A | 12/1982 | Norling et al. | .............. | 433/218 |
| 4,431,420 A | 2/1984 | Adair | .......................... | 433/199 |
| 4,433,959 A | 2/1984 | Faunce | ........................ | 433/201 |
| 4,648,845 A | 3/1987 | Orlowski et al. | ......... | 433/217.1 |
| 4,648,906 A | 3/1987 | Porteous et al. | ............... | 106/35 |
| 4,668,193 A | 5/1987 | Burgess et al. | ........... | 433/222.1 |
| 4,741,699 A | 5/1988 | Kosmos | ................... | 433/203.1 |
| 4,744,757 A | 5/1988 | Adair et al. | ................ | 433/180 |
| 4,940,676 A | 7/1990 | Evans | .......................... | 501/16 |
| 5,049,190 A | 9/1991 | Gobel et al. | ................... | 106/35 |
| 5,118,296 A * | 6/1992 | Eldred | ......................... | 433/223 |
| 5,217,375 A | 6/1993 | Oden et al. | ................. | 433/218 |
| 5,228,907 A | 7/1993 | Eppinger et al. | ............... | 10/35 |
| 5,609,675 A | 3/1997 | Noritake et al. | .............. | 106/35 |
| 6,183,256 B1 | 2/2001 | Fisher et al. | ................ | 433/219 |

* cited by examiner

*Primary Examiner*—Melba Bumgarner
(74) *Attorney, Agent, or Firm*—Douglas J. Hura; James B. Bieber; Daniel W. Sullivan

(57) ABSTRACT

A dental construct according to the present invention includes a glass-ceramic coping having a resin composite material in the form of a veneer bonded or otherwise affixed to at least a portion of the coping. A method according to the invention of preparing the dental construct includes the step of bonding or otherwise affixing a resin composite material in the form of a veneer to at least a portion of a glass-ceramic substrate coping.

23 Claims, 1 Drawing Sheet

COMPOSITE VENEERED CAST GLASS-CERAMIC DENTAL CONSTRUCT

This application is a continuation of application Ser. No. 09/838,953, filed Apr. 20, 2001; now abandoned.

FIELD OF THE INVENTION

The present invention relates to dental products and processes and, more particularly, to the fabrication of dental prosthetic devices. More particularly, the invention relates to dental prosthetic devices formed from a composite veneered cast, sintered or hot pressed glass-ceramic material.

BACKGROUND OF THE INVENTION

A major purpose of the dental profession has been to replace or correct damaged or deformed tooth structure or conditions by fabricating and installing dental constructs such as crowns, inlays, onlays, bridges (fixed partial dentures) and the like. These prostheses ideally should (1) be inert in the oral environment, (2) resist the forces of mastication, (3) be capable of assuming physiologically compatible anatomical configurations, and (4) exhibit aesthetic characteristics similar to those of natural teeth.

Present dental constructs are customarily composed of metal alloys, porcelain, amalgam, or acrylate polymers or combinations thereof, which do not completely meet the foregoing ideal requirements. Metal alloys and amalgam are undesirable in locations where aesthetics is a major consideration because they sharply differ from teeth in optical characteristics. Porcelain and acrylate polymers are either too brittle or too weak to resist masticatory forces in many locations. Composite structures, as in the case of an alloy substructure for strength and a porcelain superstructure for appearance are generally very technique sensitive and many times are very bulky. Therefore, prior dental constructs have been at best a compromise upon the four ideal requirements.

One drawback especially with the constructs employing metal alloys, is that these often release potentially toxic ions such as those from nickel in the base metal alloys. Another area with previous dental constructs have been deficient is in the ease of customizing shade and aesthetics of the material and matching the patient's existing dentition. Ceramic crowns have normally required greater involvement between the dental practitioner and the dental laboratory in order to adequately customize the shade and aesthetics. It has also been a problem that ceramic veneers are subject to fracture. A further problem encountered with the metal-ceramic veneered system is fracture of the ceramic veneer. Such a problem inevitably requires the expensive and complicated procedure of removal of the crown or bridge from the mouth in order for it to be repaired or remade by the dental laboratory. In this regard, it has been found that the greater the difference between the thermal expansion qualities of metal and that of the ceramic materials applied thereto with previous constructs, aggravate the problem of cracking or fissuring. Such problems become increasingly troublesome with the number of re-firing schedules of the ceramic-metal construct.

A need exists therefore, for a dental construct having ease of manufacture qualities. A need also exists for such a construct having improved aesthetic characteristics and bio-compatability. The constructs should be easily customized for colour shading and shape at the chair-side. In order to avoid delamination of the veneering material, the substrate and the veneering material of a dental construct should ideally not be sensitive to slight mismatch between their thermal expansion characteristics. In addition the veneering material should not be subject to failure at very low strains.

SUMMARY OF THE INVENTION

It is therefore, an object of the invention to provide a dental construct.

It is another object of the invention to provide a dental construct in the nature of a dental prosthesis.

It is a further object of the invention to provide a less expensive construct that may be easily customized for colour, shade and shape by the dental practitioner at the chair-side.

It is a further object of the invention to provide a construct which may be repaired by the dental practitioner at the chair-side, without the necessity of removing the prosthesis from the mouth.

It is an additional object of the invention to provide a chemically inert non-metallic (ceramic) substrate coping which exhibits some degree of translucency.

It is still another object of the invention to provide a non-metallic dental construct having improved aesthetic characteristics.

It is still yet a further objective of the invention to provide a veneer for a dental construct having improved toughness characteristics.

It is still yet an additional object of the invention to provide a dental construct which avoids the necessity of close matching of the thermal expansion characteristics of the substrate and the veneering material.

In general, a dental construct according to the present invention comprises a glass-ceramic coping having a resin composite material in the form of a veneer bonded or otherwise affixed to at least a portion of the coping.

A method according to the invention of preparing the dental construct comprises the step of bonding or otherwise affixing a resin composite material in the form of a veneer to at least a portion of a glass-ceramic substrate coping.

These and other objects of the present invention, which shall become apparent from the description in claims to follow, are accomplished by the invention hereinafter described and claimed.

PREFERRED EMBODIMENTS FOR CARRYING OUT THE INVENTION

Figure 1:
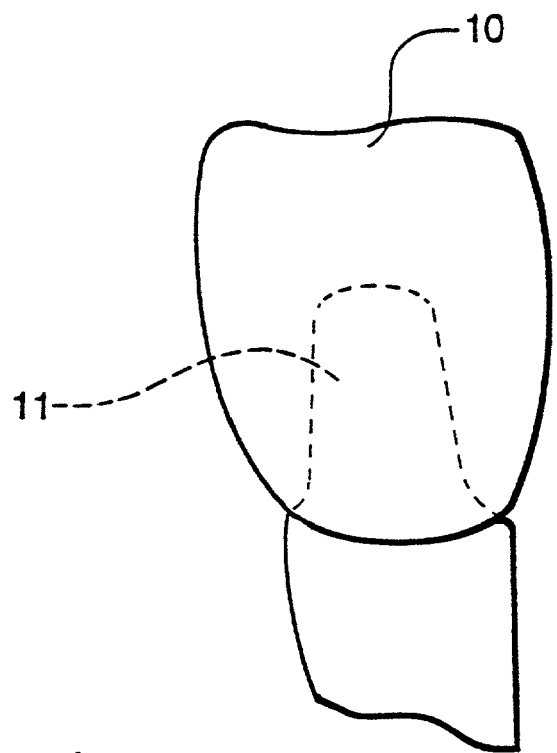
FIG. 1 is a close-up, front elevational view of one dental construct according to the invention, namely a dental crown on a prepared tooth, the prepared portion of the tooth being shown in phantom lines.

There is provided according to the present invention, a dental construct having a glass-ceramic base or coping and a resin composite material in the form of a veneer bonded to the coping. The dental construct can be without limitation, a crown or bridge (fixed denture) restoration such as anterior or posterior crowns and bridges, Maryland-type bridges, onlays, inlays or any other type of dental restoration or appliance. The invention will be exemplified herein with respect to a crown 10 as depicted in the drawing, with the understanding that any dental construct is within the scope of the invention.

By way of example, FIG. 1 depicts a prepared tooth 11 (shown partially in phantom lines) having a crown 10 affixed thereto. Crown 10 is affixed to prepared tooth 11 in any manner conventional with dental restorations, including cementatious and/or adhesive bonding.

The dental construct of the invention, such as crown 10, is preferably fabricated from a glass-ceramic material. Any method which is conventional in the art for preparing a glass-ceramic dental coping is within the scope of the invention. For example, the coping may be fabricated by being hot pressed, built-up by sintering frit using conventional methods, or by casting the glass-ceramic substructure using the lost wax casting method. An example of the fabrication of a glass-ceramic dental product is described in U.S. Pat. No. 4,431,420 which is hereby incorporated by reference for such disclosure.

A commercially available example of a glass-ceramic material is DICOR® brand glass-ceramic material available from Dentsply International Inc., York, Pa. It is known to be a tetrasilic-micaglass-ceramic $K_2O$—$MgF_2$—$MgO$—$SiO_2$.

Preferred glass-ceramic materials are $Li_2O$—$CaO$—$Al_2O_3$—$SiO_2$—X, $Al(PO_3)_3$—$SiO_2$—$Li_2O$—$CaX$ and $Li_2O$—$ZnO$—$P_2O_5$—X, where X is a network modifier such as $TiO_2$, $ZrO_2$, $La_2O_3$, $CeO_2$, $Y_2O_3$, $ZnO$, $MgO$, $BaO$, $PbO$, $Ta_2O_5$, $Li_2O$, $K_2O$, $CaF_2$, $MgF_2$, $AlF_3$, $BaF_2$, and $Na_2O$. Such materials are preferably synthesized by wet chemical methods such as 1) Sol-gel polymerization of prehydrolyzed alkoxides (some soluble metal salts may be added becoming complexed into the gel). 2) The precipitation of precursors from suspensions by spray-drying, spray-freeze drying or freeze-drying. 3) Room temperature or elevated aqueous solution precipitation synthesis methods. 4) Hydrothermal synthesis in which the aqueous solutions or suspensions of precursor materials are heated at elevated temperatures and pressures. 5) Organic solution synthesis precipitation methods, and 6) Glycothermal synthesis in which the organic solutions or suspensions of precursor materials are heated at elevated temperatures and pressures. These methods allow homogeneous glasses and ceramics to be formed at temperatures well below the normal temperature required to sinter high density bodies of uniform microstructure.

Such compositions can be produced to allow them to be cast using the lost wax-casting process. A wax replica of the coping is produced sprued and invested in a refractory mold material, typically a silica refractory with a phosphate bonding agent is preferred. The burnout temperature for the mould is typically about 900° C., which should be heat soaked for at least 40 minutes prior to casting. The silica refractory is preferably in the form of amorphous silica and quartz rather than cristobalite. A lower compensation is required for the contraction of the glass on cooling following casting compared to a metal structure. The glass compositions identified above can be cast at temperatures from about 1,150 to about 1,450° C., and can be cerammed at temperatures between about 510 to 1200° C. depending upon the composition. These materials possess good mechanical properties such as: modulus of elasticity values of 95–115 GPa compared to conventional dental porcelain which has a modulus of 65–75 GPa, fracture toughness values of between 1.2 and 1.8 $K_{1C}$ (MPa m½) and 'True Hardness' values of between 3.5 to 5.9 GPa.

A preferred method of casting the cerammable glass materials involves the use of an induction process to melt the glass or glass-ceramic starting material. A conducting insert is employed in the melting crucible to allow melting of the non-conducting glass to take place. A graphite or platinum insert is placed within the refractory crucible. The castings are removed from the investment mould by hand and lightly gritblasted with 25 μm alumina grains. Following the casting of the glass in the desired shape of the coping, such as the crown depicted as in FIG. 1, the glass material is subjected to a controlled crystallization (ceramming) by a conventional heat treatment procedure. For example the cast construct (coping) is exposed to a temperature of 850° C. for 30 minutes. The precise ceramming temperature for each glass composition has to be determined from the thermal analysis (DTA, curve). The heating can be performed in a gas fired or electric furnace with appropriate temperature control (±5° C.).

According to the invention, the cerammed coping is then coated or at least partially coated, with a resin composite material in the form of a veneer, and contoured and shaped to simulate a natural tooth. Any composite material that is appropriate for use in the oral cavity is within the scope of the invention for use as the veneer coating. Preferred veneering materials include composites with dimethacrylate matrix resins. These matrix resins are generally mixtures of BIS-GMA and TEGDMA, in many commercial material, however urethane dimethacrylates and large oligomeric structures of BIS-GMA-urethanes may also be used.

Such composite materials having a blend of glass or ceramic particles dispersed in a polymerizable synthetic organic resin matrix. The polymer materials being blended together with finely divided inorganic (filler) reinforcing phase such as a calcium aluminosilicate, zirconium silicate, barium or strontium aluminosilicate glass or ceramics, preferably having a blending of large and small particles (0.04 to 10 μm) to obtain optimum packing density and mechanical properties. The so called hybrid systems may have either a bimodal or in some cases a trimodal blend of particle size. The trimodal systems lend themselves to a greater loading density. The size and distribution of the filler particles and the refractive index of filler and matrix resin should be optimized to give appropriate translucence for natural aesthetic results.

The filler particles of such composites preferably are surface treated to provide adhesion between the resin matrix and the glass or ceramic filler particles. Adhesion being achieved by using a silane (organo functional adhesion promoter) treatment. Most composite systems contain 2–5% of fumed silica to adjust viscosity and handling characteristics. This sub-micron silica is also generally treated with a silane coupling agent to reduce the uptake of water by the large surface area.

Such composite materials may use photopolymerizing systems activated by visible light in which a light sensitive absorber such as camphorquinone is used together with an aliphatic amine accelerator. However, chemically activated composite systems using the N,N-dimethyl-para-toluidine and benzoyl peroxide or similar system for chemical activation will be very appropriate, as will the heat curing systems since the veneering process is fabricated as an indirect system outside the mouth.

It is preferred, although not necessarily required, to prepare the coping to receive the veneer. For example, the coping may be etched by being physically contacted with a solution of hydrofluoric acid from 5 to 15 seconds (depending on the composition of the ceramic) to produce a micromechanical retentive surface. Cleaning of the ceramic surface with isopropyl alcohol, acetone or phosphoric acid is preferable, prior to silane treatment.

The etched and clean surface should preferably be treated with a coupling agent such as a hydrolyzed solution of aminopropoxyltriethoxy methacrylates silane or 3-(methoxyloxypropyl)-trimethoxysilane. A phosphoric acid solution can be added to the silane coupling agent to hydrolyse it prior to application on the ceramic surface. Alternatively a dilute solution of activated silane with ethyl alcohol can be used. The clean etched cerammed coping surface is then coated with the silane solution and dried for 30 minutes to one hour at 60° C.

The glass-ceramic coping will typically be from about 0.4 to about 1.00 mm in thickness. Greater thickness will be required in situations of higher masticatory stress (biting force). The overall combined thickness of coping and veneer will be dictated by function and aesthetics. However, typically the veneer would range from about 0.2 to as high as about 2.00 mm. The viscosity of the veneering resin (which may be as high as 100,000 cp or more) may be too high to allow good wetting of the surface of the silane treated ceramic coping substrate. The viscosity of the first coating of veneer can be reduced if necessary by use of low molecular weight monomer dimethacrylate diluents, such as ethylene glycol dimethacrylate (3.40 cp). In order to build up the veneer coating to the desired shape, thickness, contour and translucency/colour combination, a layering technique will be appropriate. Through subsequent applications the desired result can be obtained. In the case of photopolymerizing resin systems, curing can be accomplished at various stages of the build up. Natural tooth characteristics of translucency and colour can be incorporated during the sequential build up process.

It will be appreciated by one skilled in the art that a veneered structure according to the present invention has the strength, toughness and molulus of elasticity of a glass-ceramic structure with good marginal fit, combined with a tough composite coating which can be easily fabricated, with the option of adjustment of aesthetics and repair even when in place in the patient's mouth.

Figure 2:
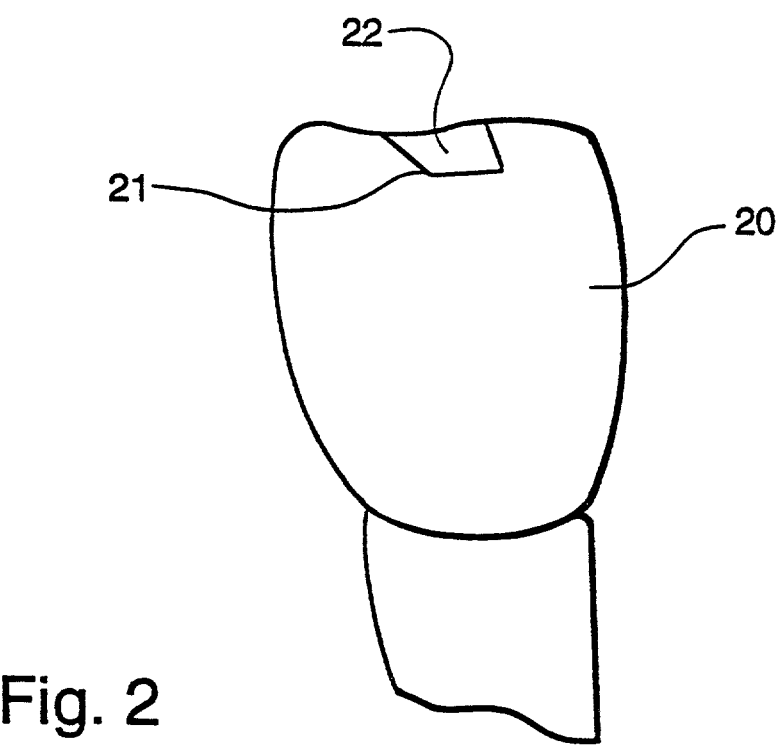
FIG. 2 is an alternative embodiment of a dental construct according to the invention.

According to another aspect of the present invention, an inlay is prepared having a hollow cavity therein. As shown in FIG. 2, tooth 20 is prepared to receive an inlay 21. That is, most likely, tooth 20 will have had a damaged or decayed area (not shown) removed by conventional dental techniques. Inlay 21 having an open area 22 therein is formed according to any technique as was discussed above, and in the shape of the excavated area of tooth 20. Inlay 21 may be referred to as a "hollow box inlay". The cerammed, etched and silane treated hollow box inlay 21 is cemented or otherwise affixed to tooth 20 by conventional techniques. The relatively stiff ceramic supports the tooth 20 at the margins. The open area 22 of hollow box inlay 21 is then filled with a resin material such as a dimethacrylate as was discussed hereinabove. It will be appreciated that when worn, the resin material can be easily replaced while the margins will remain intact supported by the stronger and more rigid ceramic.

It will also be appreciated that an advantage of the present invention over previous dental constructs is the ability of the dental practitioner to customize the color (shade and physical aesthetics) of the veneering material. The veneer can also be easily repaired, chanced or replaced with a subsequent veneer at the chair-side by the dental practitioner.

General Experimental

In order to demonstrate the practice of the present invention, a number of examples of dental constructs have been prepared.

Several experimental glass/ceramic formulations have been successfully cast and cerammed in the form of constructs (copings) for dental crowns. This glass-ceramics had a general composition in the system $SiO_2$—$Al_2O_3$—$La_2O_3$—$CeO_2$—$CaO$—$Li_2O$. Examples of the glass-ceramic formulations are illustrated in table 1

TABLE 1

Examples of Compositions of Castable Glass-Ceramic Materials

| Materials | % $SiO_2$ | % $Al_2O_3$ | % $La_2O_3$ | % $CeO_2$ | % $CaO$ | % $Li_2O$ |
|---|---|---|---|---|---|---|
| NAB/CG/7c | 44 | 16 | 23 | 6 | 5 | 6 |
| NAB/CG/10a | 59 | 12 | 13 | — | 8 | 8 |
| NAB/CG/10b | 49 | 12 | 23 | — | 8 | 8 |
| NAB/CG/L1 | 44 | 16 | 38 | — | 2 | — |
| NAB/CG/L3 | 36 | 16 | 46 | — | 2 | — |
| NAB/CG/L4a | 32 | 16 | 50 | — | — | 2 |
| NAB/CG/L5 | 30 | 15 | 53 | — | 2 | 7 |

The reduction to practice has been achieved by examples of these castings being veneered with a ceramic/resin composite material to produce crowns with acceptable aesthetics. The development of the idea of an induction melting casting technique for the glass proved to be an excellent procedure with first class results. Sections as thin as 200 μm have been successfully cast. Four of the different glass/ceramic formulations which have been cast have been found to have excellent mechanical properties which are much better than the commercial castable glass-ceramic materials currently available as indicated in Table 2. The highest fracture toughness and the second highest true hardness was exhibited by NAB/CG/7c which also had the lowest thermal expansion coefficient. A low thermal expansion coefficient is desirable since less compensation has to be made for the thermal shrinkage which occurs following cooling down after casting. The softening temperatures ranged from 863 to 1075° C. for these materials. The thermal coefficient of expansion values for the examples shown in Table 2 ranged from 2.03 to 5.88×10$^{-6}$/° C. All of the formulations were cerammable (capable of precipitating crystalline phases following heat treatment) which resulted in a significant increase in the values for mechanical properties such as fracture toughness and modulus of elasticity.

TABLE 2

Examples of Properties for Castable Glass-Ceramic Materials

| Materials | Softening Temperature °C. | Coefficient Thermal Exp. 30–400 10X–6/° C. | Fracture Toughness K1$_c$MPa.m$^{0.5}$ | True Harness H° GPa | Young's Modulus GPa |
|---|---|---|---|---|---|
| NAB/CG/7c | 975 | 2.03 ± 0.08 | 1.78 ± 0.02 | 5.57 ± 0.36 | 116.19 ± 0.42 |
| NAB/CG/10a | 863 | 3.90 ± 0.05 | 1.60 ± 0.02 | 4.45 ± 0.20 | 96.11 ± 0.2 |
| NAB/CG/10b | 863 | 4.95 ± 0.09 | 1.44 ± 0.02 | 4.66 ± 0.35 | 112.09 ± 0.83 |
| NAB/CG/L1 | 1063 | 4.72 ± 0.33 | 1.30 ± 0.02 | 4.86 ± 0.07 | 90.89 ± 0.69 |
| NAB/CG/L3 | 1025 | 5.38 ± 0.28 | 1.35 ± 0.01 | 5.14 ± 0.10 | 96.18 ± 0.25 |
| NAB/CG/L4a | 1013 | 5.88 ± 0.15 | 1.13 ± 0.02 | 5.09 ± 0.08 | 111.48 ± 0.57 |
| NAB/CG/L5 | 1075 | 5.83 ± 0.10 | 1.44 ± 0.02 | 5.78 ± 0.90 | 113.08 ± 0.41 |
| Dicor ™(as cast) | | | 1.12 ± 0.01 | | 63.79 |
| Dicor ™(Cerammed) | | | 1.22 ± 0.02 | | 64.63 |

It will therefore, be appreciated that a dental construct according to the present invention accomplishes the objects of the invention as set forth above, and otherwise constitutes a novel, unique and heretofore unknown contribution to the art. The invention has been exemplified herein for illustrative purposes all possible variations beyond the best mode have not necessarily been set forth. The complete scope of the invention shall be limited only by the claims set forth and not be the examples as provided. One skilled in the art will readily appreciate that components, process conditions and the like can be varied from those set forth and still fall within the scope of the invention.

What is claimed is:

1. A dental construct comprising a glass-ceramic coping having a resin composite material in the form of a veneer affixed to at least a portion of the coping, wherein said coping having glass-ceramic material selected from a group consisting of $Li_2O$—CaO—$Al_2O_3$—$SiO_2$—X, $Al(PO_3)_3$—$SiO_2$—$Li_2O$—CaX and $Li_2O$—ZnO—$P_2O_5$—X, where X is a network modifier selected from a group consisting of $TiO_2$, $ZrO_2$, $La_2O_3$, $Y_2O_3$, ZnO, MgO, BaO, PbO, $Ta_2O_5$, $K_2O$, $CaP_2$, $MgF_2$, $AlF_3$, $BaP_2$, and $Na_2O$.

2. The dental construct as in claim 1 wherein a matrix resin of the composite material is a dimethacrylate resin or a urethane.

3. A composite as in claim 2 wherein the matrix resin is blended with a finely divided filler material.

4. A dental construct as in claim 3 wherein the filler material is selected from a group consisting of calcium aluminosilicate, zirconium silicate, barium or strontium aluminosilicate glass and ceramics.

5. A dental construct as in claim 4 wherein said filler material has a particle size of from about 0.04 to about 10 microns.

6. A dental construct as in claim 4 wherein the filler material is surface treated to provide adhesion to the resin matrix and said filler material.

7. A dental construct as in claim 6 wherein the filler material is surface treated using a silane material.

8. A dental construct comprising a glass-ceramic coping having a resin composite material in the form of a veneer affixed to at least a portion of said coping, wherein said coping having glass-ceramic material selected from a group consisting of $Al(PO_3)_3$—$SiO_2$—$Li_2O$—CaX and $Li_2O$—ZnO—$P_2O_5$—X, where X is a network modifier selected from a group consisting of $TiO_2$, $ZrO_2$, $La_2O_3$, $CeO_2$, $Y_2O_3$, ZnO, MgO, BaO, PbO, $Ta_2O_5$, $Li_2O$, $K_2O$, $CaF_2$, $MgF_2$, $AlF_3$, $BaF_2$, and $Na_2O$.

9. A dental construct comprising a glass-ceramic coping having a resin composite material in the form of a veneer affixed to at least a portion of said coping, wherein said coping having glass-ceramic material comprising $SiO_2$, $Al_2O_3$, $La_2O_3$ and at least one additional oxide selected from the group consisting of CaO, $Li_2O$, and combinations thereof.

10. The dental construct of claim 9, wherein a sum of weight percent of $SiO_2$, $La_2O_3$, and $Al_2O_3$ in the coping is in a range of about 83 weight percent to about 98 weight percent.

11. The dental construct of claim 9, wherein a sum of weight percent of $SiO_2$ and $Al_2O_3$ in said coping is in a range of about 48 weight percent to about 71 weight percent.

12. The dental construct of claim 9, wherein a sum of weight percent of the $SiO_2$ and $La_2O_3$ in the coping is in a range of about 67 weight percent to about 83 weight percent.

13. The dental construct of claim 9, wherein the sum of weight percent of the $Al_2O_3$ and $La_2O_3$ in the coping is in a range of about 15 weight percent to about 50 weight percent.

14. The dental construct of claim 9, wherein a weight percent of said at least one additional oxide is in a range of about 2 weight percent to about 16 weight percent.

15. The dental construct of claim 9, wherein said at least one additional oxide comprises at least CaO and wherein a sum of the weight percent of CaO and the $La_2O_3$ in the coping is in a range of about 21 weight percent to about 50 weight percent.

16. The dental construct of claim 9, wherein the at least one additional oxide comprises at least $Li_2O$ and wherein the weight percent of the $Li_2O$ in the coping is in a range of about 2 weight percent to about 8 weight percent.

17. The dental construct of claim 16, wherein $Li_2O$ comprises about 2 weight percent to about 3 weight percent of the glass-ceramic material.

18. The dental construct of claim 9, wherein the weight percent of the $La_2O_3$ in the coping is in a range of about 13 weight percent to about 50 weight percent.

19. The dental construct of claim 9, wherein a true hardness of said coping is in a range of about 4.25 H° GPa to about 5.93 H° GPa.

20. The dental construct of claim 9, wherein a modulus of elasticity of said coping with respect to Young's modulus is in a range of about 90.20 GPa to about 116.61 GPa.

21. The dental construct of claim 9, wherein a coefficient of thermal expansion of said coping from about 30° C. to about 400° C. is in a range of about $1.95 \times 10^{-6}$/° C. to about $6.03 \times 10^{-6}$/° C.

22. The dental construct of claim 9, wherein the additional oxide comprises less than 3 weight percent of the glass-ceramic material.

23. A dental construct comprising a glass-ceramic coping having a resin composite material in the form of a veneer affixed to at least a portion of said coping, wherein said coping having glass-ceramic material comprising $SiO_2$, $Al_2O_3$, $La_2O_3$ and at least one additional oxide selected from the group consisting of CaO, $Li_2O$, and combinations thereof, the dental construct further having a hollow cavity formed by the coping material, the hollow cavity comprising a hollow box inlay containing a resin material having a composition that is not identical to the composite material.

* * * * *